(12) United States Patent
Okulla et al.

(10) Patent No.: US 8,146,738 B2
(45) Date of Patent: Apr. 3, 2012

(54) APPARATUS FOR ACCOMMODATING EXCHANGEABLE CONTAINERS AND METERING MEDIA

(75) Inventors: Kai Okulla, Werdohl (DE); Michael Heidan, Engenhahn (DE)

(73) Assignee: Duo Care GmbH & Co. KG, Herscheid (DE)

( * ) Notice: Subject to any disclaimer, the term of this patent is extended or adjusted under 35 U.S.C. 154(b) by 0 days.

(21) Appl. No.: 12/757,822

(22) Filed: Apr. 9, 2010

(65) Prior Publication Data

US 2010/0258472 A1 Oct. 14, 2010

(30) Foreign Application Priority Data

Apr. 9, 2009 (DE) .......................... 10 2009 016 715
Jul. 6, 2009 (DE) .......................... 10 2009 031 964
Jul. 17, 2009 (DE) .......................... 10 2009 033 785

(51) Int. Cl.
B65D 83/00 (2006.01)

(52) U.S. Cl. .......................... 206/229; 206/38; 220/915

(58) Field of Classification Search .................. 206/223, 206/581, 229, 38, 438, 525; 220/915
See application file for complete search history.

(56) References Cited

U.S. PATENT DOCUMENTS

| 3,307,902 | A | * | 3/1967 | Nardi | 312/31.3 |
| 3,465,905 | A | | 9/1969 | Schottanes | |
| 4,193,525 | A | * | 3/1980 | Sommers | 224/414 |
| 4,334,642 | A | * | 6/1982 | Reisch | 224/461 |
| 4,345,704 | A | * | 8/1982 | Boughton | 224/414 |
| 4,600,111 | A | * | 7/1986 | Brown | 215/6 |
| 5,887,774 | A | * | 3/1999 | Bethune | 224/414 |
| 6,053,401 | A | * | 4/2000 | Andrews, Sr. | 229/117.3 |
| 6,145,685 | A | * | 11/2000 | Dick | 220/23.88 |
| 7,300,171 | B2 | * | 11/2007 | Sutton | 362/101 |
| 7,350,520 | B1 | | 4/2008 | Richard-Bey | |
| 2003/0127354 | A1 | | 7/2003 | Chen | |
| 2009/0223999 | A1 | * | 9/2009 | Hill et al. | 222/129 |

FOREIGN PATENT DOCUMENTS

EP 0841262 5/1998

OTHER PUBLICATIONS

European Search Report, European Patent Application No. 10001623, dated Sep. 15, 2010.

* cited by examiner

*Primary Examiner* — Jacob K Ackun

(74) *Attorney, Agent, or Firm* — Michael Best & Friedrich LLP

(57) ABSTRACT

An apparatus for accommodating different exchangeable containers comprising at least two separated and closable internal spaces arranged on a common longitudinal axis. The apparatus is characterized in that the internal spaces are respectively closed by a functional lid.

17 Claims, 10 Drawing Sheets

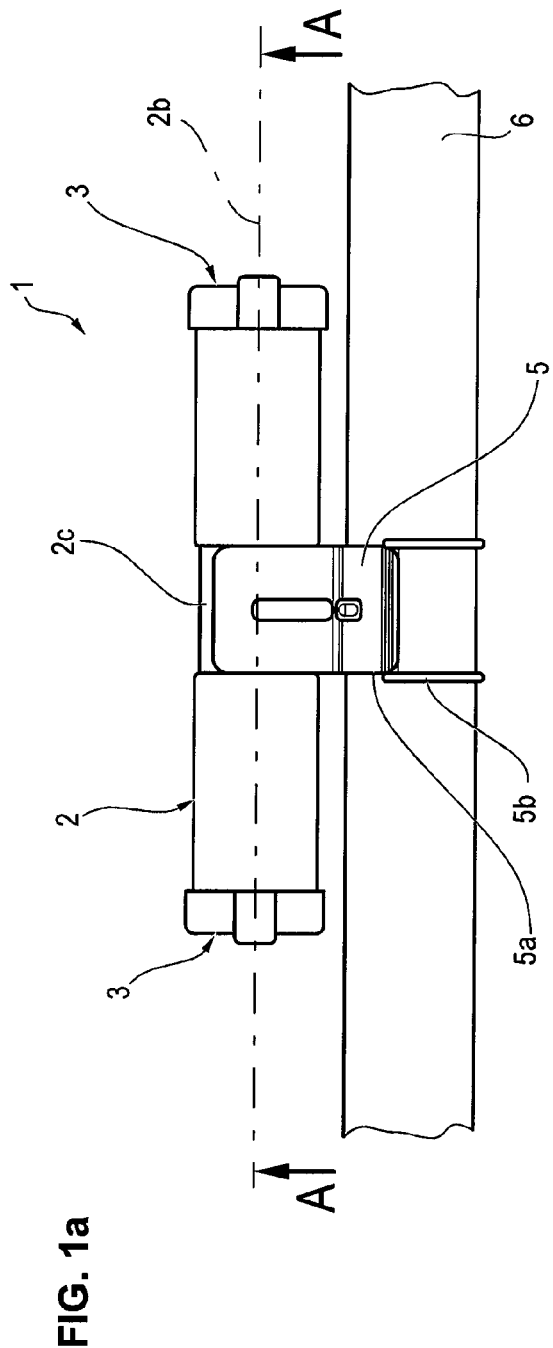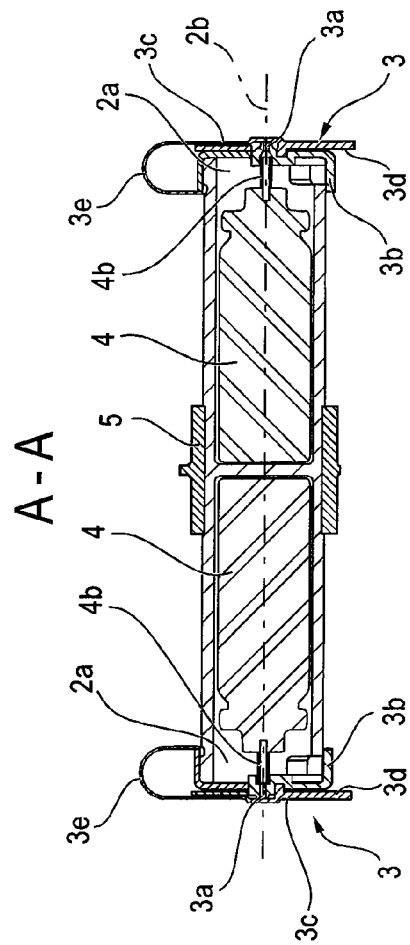
FIG. 1a
FIG. 1b

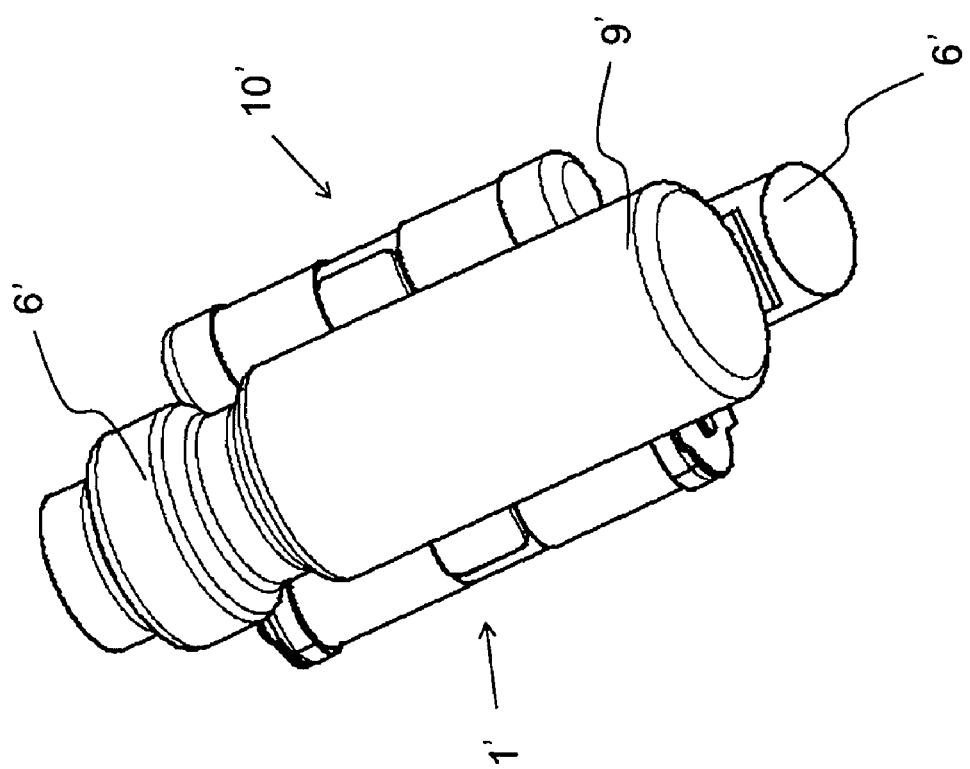

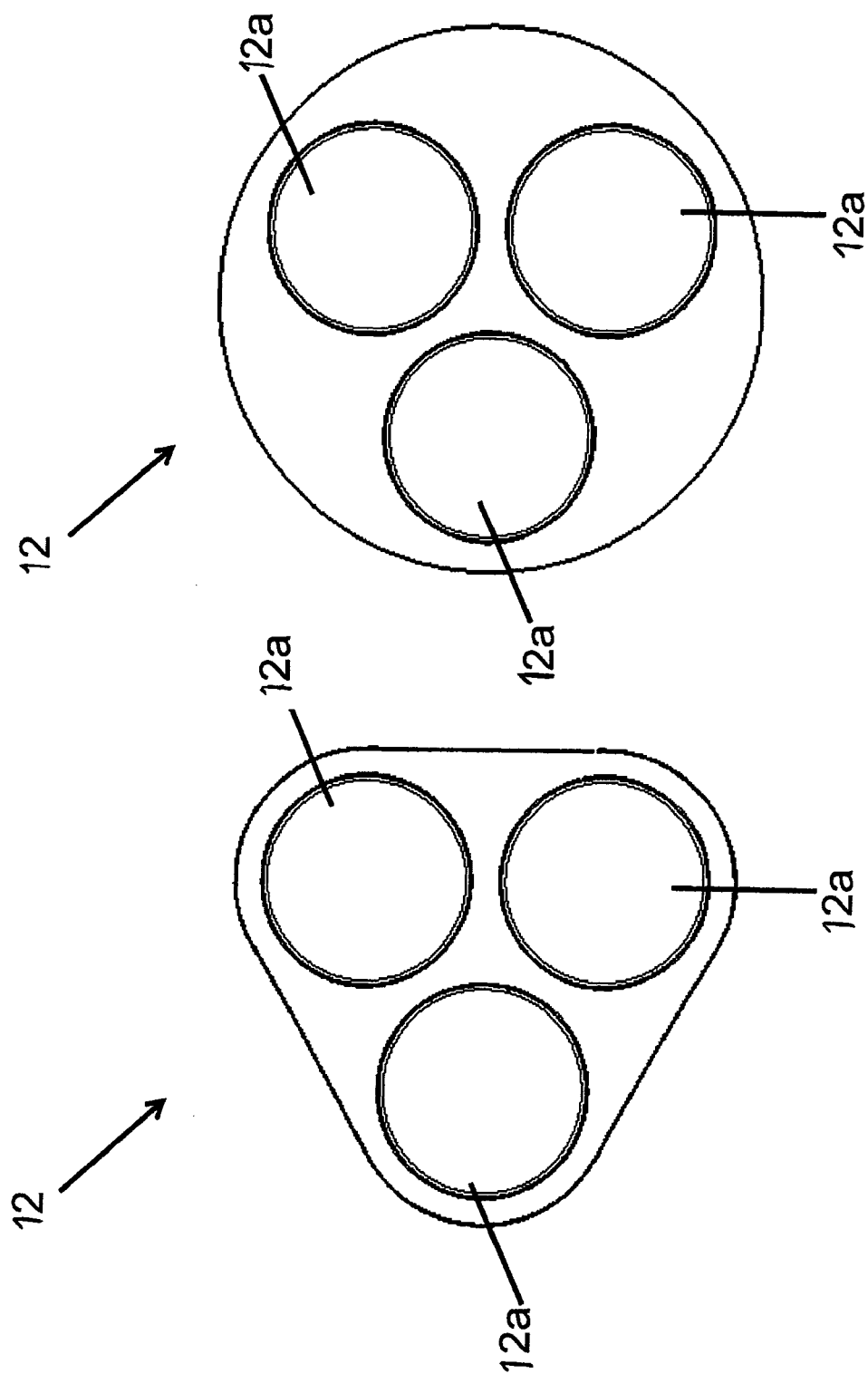

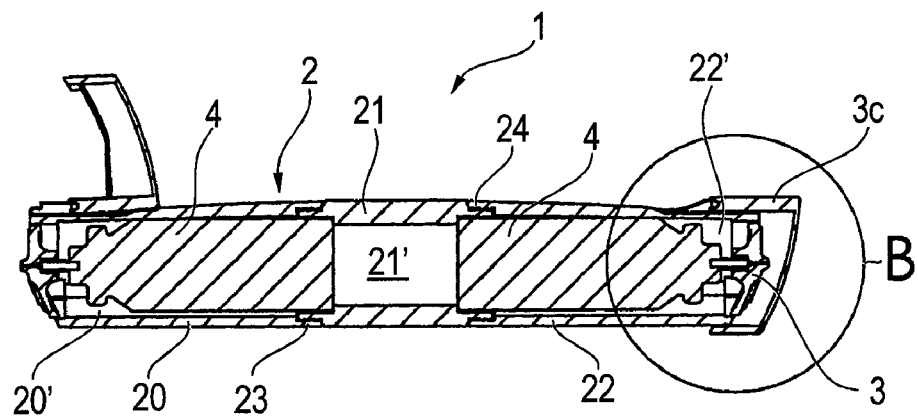
FIG. 11
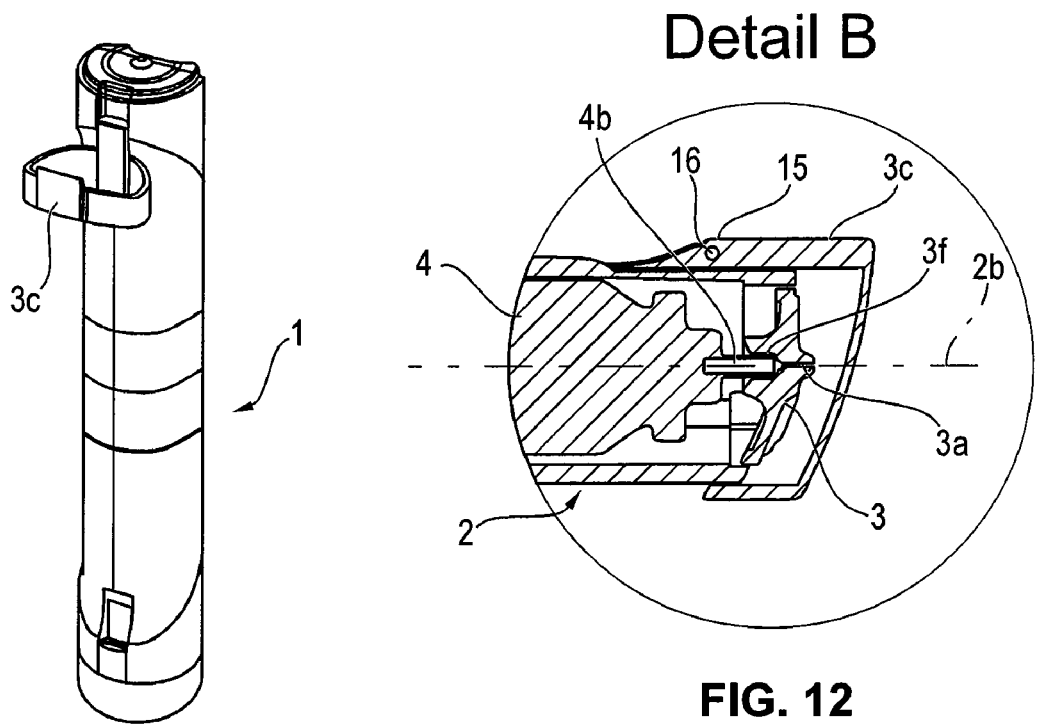
FIG. 10
FIG. 12

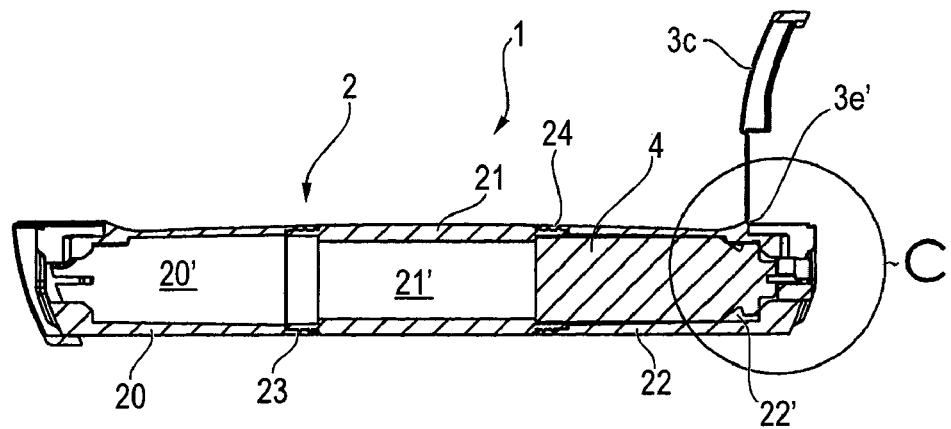
FIG. 14
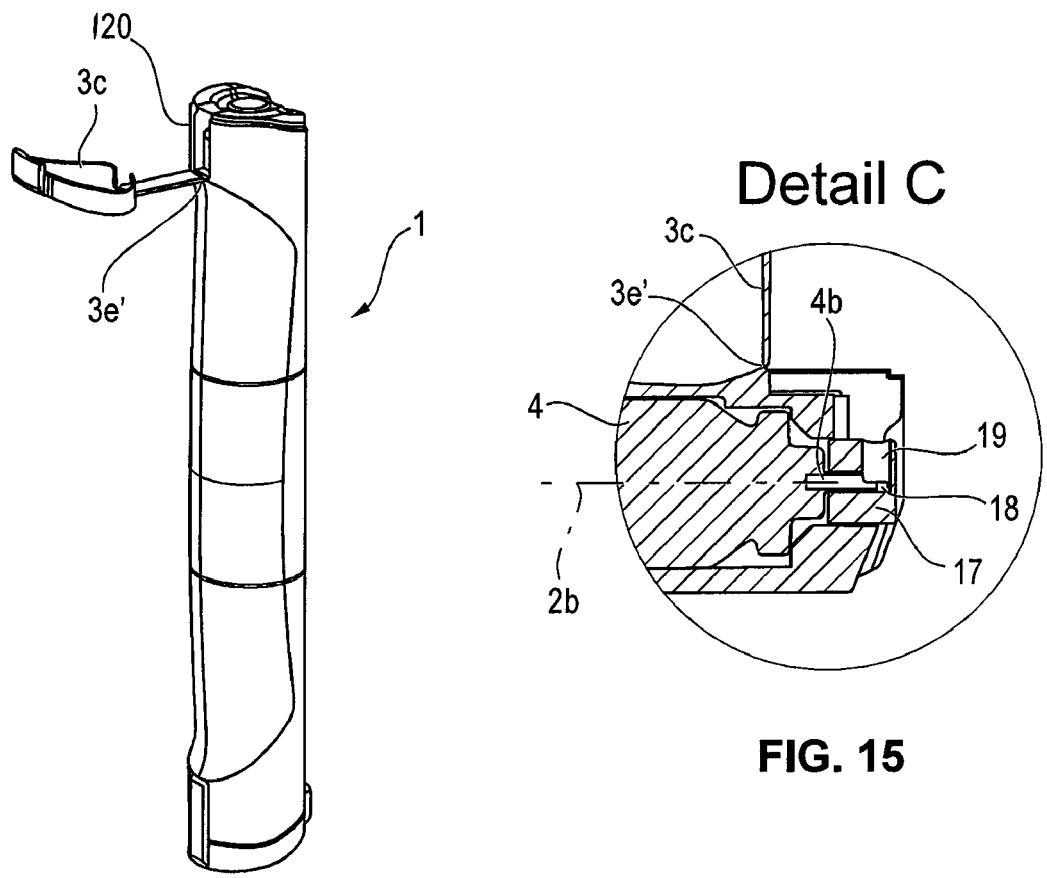
FIG. 13
FIG. 15

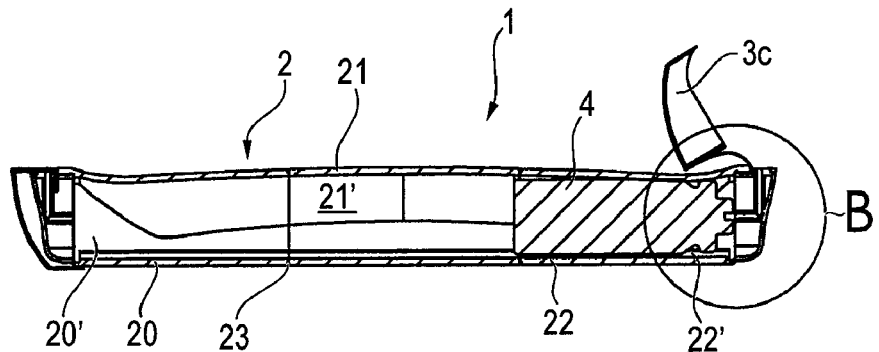
FIG. 17
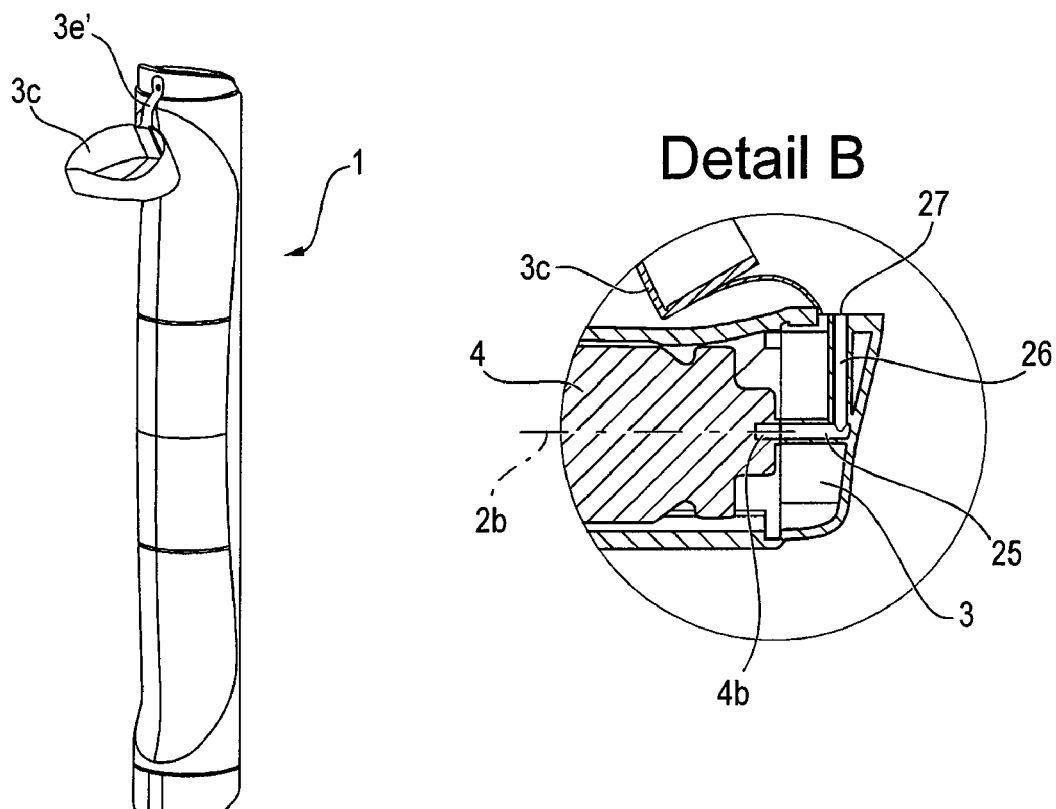
FIG. 16
Detail B
FIG. 18

APPARATUS FOR ACCOMMODATING EXCHANGEABLE CONTAINERS AND METERING MEDIA

CROSS REFERENCE TO RELATED APPLICATIONS

This application claims the benefit of and priority to: German Patent Application No. 102009031964.6, filed on Jul. 6, 2009; and to German Patent Application No. 102009033785.7, filed Jul. 17, 2009; and to German Patent Application No. 102009016715.3, filed Apr. 9, 2009. German Patent Application No. 102009033785.7, filed Jul. 17, 2009, claims the benefit of German Patent Application No. 102009016715.3, filed Apr. 9, 2009.

BACKGROUND

The invention relates to an apparatus for accommodating different exchangeable contents and/or containers.

When participating in outdoor activities, such as for hiking or cycling, injuries may easily occur. Such injuries may require the use of disinfection agents and liquid patches that ordinarily are carried separately.

SUMMARY

The present invention relates to an apparatus for accommodating different exchangeable contents and/or containers and comprises at least two separated and closable internal spaces. The internal spaces are arranged on a common longitudinal axis and are closed by functional lids. The functional lids are arranged on the ends of the apparatus and have openings through which the different media may escape from the containers. The openings are closed by additional covers.

The exchangeable containers may be, for example, spraying bottles which contain media that can be sprayed.

The mentioned spraying bottles may include, for example, disinfection agents, means for attending to lesions or cleaning same and sprayed patches as well as cooling agents. The apparatus may thus be used as an emergency set in case of injuries.

To promote simple handling, the apparatus is formed as a simple handle that can be used with one hand, wherein the cover may, fore example, be lifted at a flap by means of the thumb in order to release the functional lid. The functional lid may also enable actuation of the spray pin of the spraying bottle in order to spray the medium.

To promote versatility, different adapter possibilities are provided. Hence, it is possible to carry the device around a belt or to attach it to a bicycle. The apparatus can be used, for example, outdoors, such as for hiking or cycling, where injuries may easily occur that require the use of disinfection agents and liquid patches. The apparatus is small, can be handled easily and is therefore easily portable. Many other possibilities of use with different media are feasible, such as for animals or also for craftspeople.

In some embodiments, the apparatus for accommodating different exchangeable containers comprises a handle which comprises at least two separated and closable internal spaces which are arranged on a common longitudinal axis. Each internal space is closed by a respective functional lid.

Preferably, the at least one functional lid comprises an opening through which the medium within the containers may escape.

A further advantage is that the functional lid comprises a lid insert which actuates the spray pin of, for example, an aerosol can upon being actuated, such that the medium can escape and may be metered.

In some embodiments, the at least one functional lid can be closed by a cover, such that the opening is protected against things like dirt or damage. In this case, the functional lid is movably connected to the cover, such as by an integral hinge.

In certain embodiments, the handle comprises an adapter receptacle at which an adapter can be attached.

In some such embodiments, the adapter comprises a further receptacle.

In other embodiments, the present invention relates to an emergency set for accommodating different exchangeable contents and comprises a handle having three separated and closable internal spaces. The internal spaces are arranged on a common longitudinal axis. The center internal space can be opened and closed by a fastener. This fastener may be formed, for example, as a screw plug or a clip.

The exchangeable contents may be different combinations of means for first aid in case of accidents and for injuries. For example, two spraying bottles including disinfection agents or liquid patches can be combined with a safety vest or a gauze bandage.

A further possibility includes various combinations of contents and containers. For example, an emergency set and a further knapsack can be attached to bicycles by means of an adapter near a drinking bottle.

It should be appreciated that the fields of application with respect to emergency sets are many, and are mentioned herein only as examples.

In some embodiments, the emergency set may contain different exchangeable contents and comprises a handle having three separated and closable internal spaces which are arranged on a common longitudinal axis, wherein the handle can be opened and closed at its center internal space by a fastener.

In some embodiments, the fastener is provided as a thread.

In other embodiments, the fastener is provided as a clip.

In some embodiments, a safety vest is included in the center internal space.

In other embodiments, a gauze bandage is included in the center internal space.

In some embodiments, the adapter may accommodate an emergency set as well as at least one additional knapsack.

In other embodiments, the adapter may accommodate an emergency set, a knapsack as well as a drinking bottle.

According to some embodiments, the present invention relates to an apparatus for accommodating different exchangeable containers and comprises at least two separated and closable internal spaces. The internal spaces are arranged in a kind of accommodating body which may be compared to the cylinder of a revolver. In this case, the internal spaces may also be arranged in duplicate. In such an embodiment, respectively two internal spaces are arranged on a common longitudinal axis. This embodiment would be comparable to a double cylinder. Each internal space is separately closed by a functional lid. The functional lids are disposed on the ends of the internal spaces and have openings through which the different media may escape from the containers. The openings are closed by additional covers to avoid contamination.

The exchangeable containers may be spraying bottles containing media which can be sprayed. The covers are so-called functional lids. The two-part functional lid, for example, enables the actuation of the spray pin of the spraying bottle to spray the medium and also functions to close the opening of the spray pin.

In order to be able to use the apparatus in various ways, different configurations are provided. It is possible to fill the apparatus differently, depending on the purpose of use. The handling may also be adapted through the use of suitable attachment or carrying means.

The emergency set box may be extended such that the shape and the arrangement of the internal spaces can be designed as desired. For example, a double cylinder shape also is provided, in which internal spaces having functional lids are arranged on both ends.

The emergency set box can be used e.g. outdoors, such as for hiking or cycling. In these cases, injuries may easily occur, which require the use of disinfection agents and liquid patches. In addition, the emergency set box may also accommodate a safety vest for cyclists. Many other uses are possible, and these examples should not be regarded as limiting. The apparatus is small, can be handled easily and is therefore easily portable. Many other uses with different media are feasible, such as for animals or also for craftspeople.

One advantage is that the emergency set box for accommodating different exchangeable containers is made of a base body comprising at least two separated and closable internal spaces which are arranged side-by-side and are respectively closed by a functional lid.

In one embodiment, the functional lid comprises at least one opening through which the medium inside the containers can escape.

In another embodiment, the functional lid comprises a cover.

In another embodiment, the at least one internal space may accommodate components of an emergency kit.

In a further embodiment, the internal spaces of the base body are arranged about a common axis.

In a still further embodiment, the base body forms a triangle.

In a still further embodiment, the base body forms a circle.

In one variation, the base body is doubled by providing a second base body facing opposite a first base body.

BRIEF DESCRIPTION OF THE DRAWINGS

In the drawings, the subject-matter of the invention is shown schematically and is described in the following detailed description with reference to the figures, wherein like components have like reference numerals.

FIG. 1a is a plan view of the apparatus.

FIG. 1b is a sectional view taken along line A-A of FIG. 1a.

FIG. 2 is an isometric exploded view of the apparatus of FIG. 1a.

FIG. 3a is an isometric exploded view of an emergency set.

FIG. 3b is a sectional view of the emergency set of FIG. 3a.

FIG. 5 is a further isometric view of the emergency set.

FIG. 8 illustrates a triangle shaped base body for the inventive emergency set box FIG. 9 illustrates a circular shaped base body for the inventive emergency set box.

FIG. 10 is a perspective view of a further embodiment of the apparatus in the form of an emergency set box.

FIG. 11 is a sectional view of the embodiment illustrated in FIG. 10.

FIG. 12 illustrates detail B of FIG. 11 in an enlarged view.

FIGS. 13 to 15 show illustrations, analogous to FIGS. 10 to 12, of a further embodiment of the apparatus.

FIGS. 16 to 18 show illustrations, analogous to FIGS. 10 to 12, of a further alternative embodiment of the apparatus.

DETAILED DESCRIPTION

Figure 2:
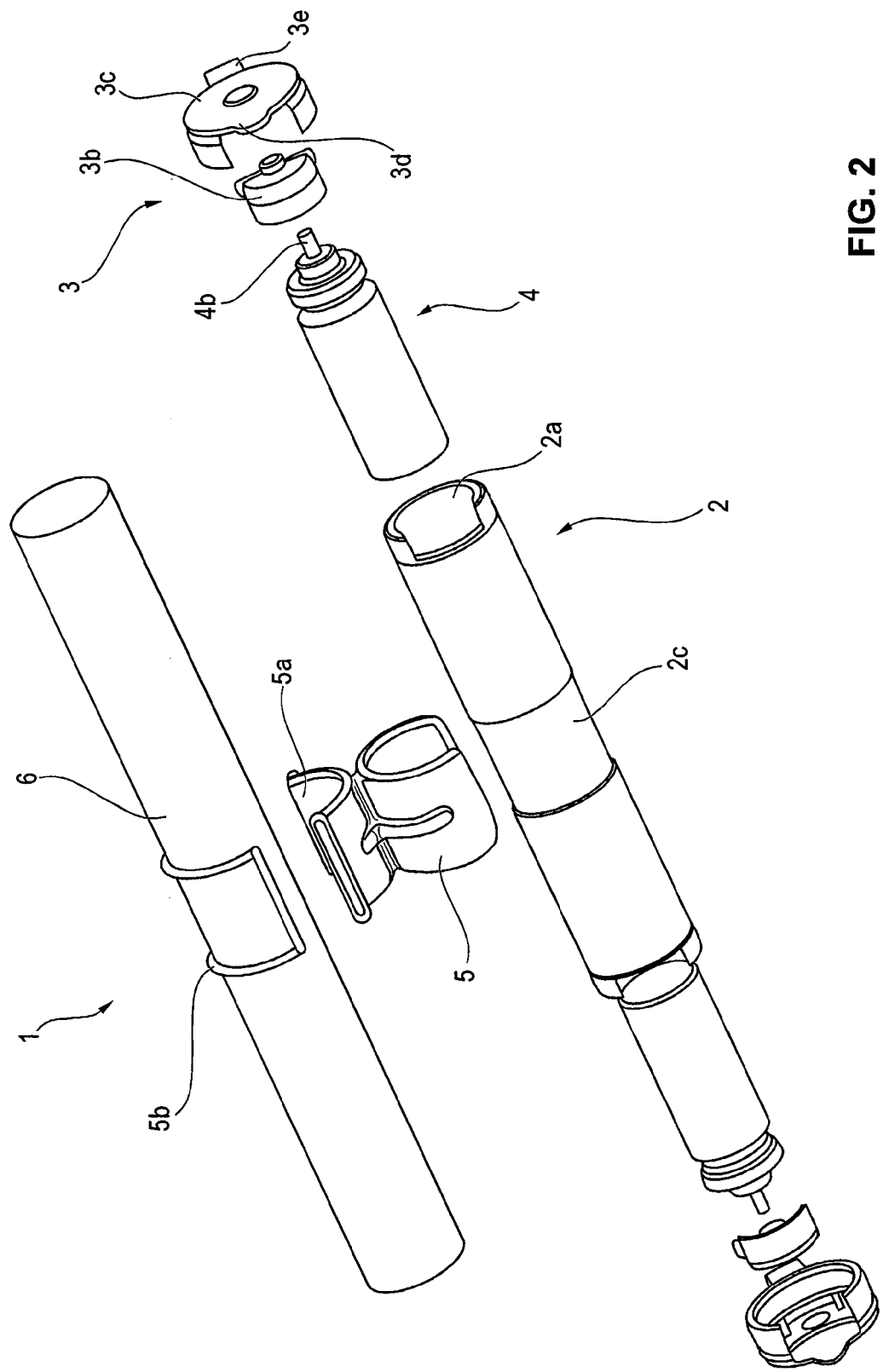

FIG. 1a shows an overall view of an apparatus for accommodating different exchangeable contents and/or containers 1. The apparatus 1 defines a longitudinal axis 2b and is attached to a pipe 6 by means of an adapter 5. The pipe 6 is, for example, part of a bicycle frame. The adapter 5 comprises a further receptacle 5a which surrounds the pipe 6 together with an additional part 5b. The other side of the adapter 5 partially encompasses a handle 2 at an adapter receptacle 2c. Therewith, the apparatus 1 is secured against axial and radial displacement. Functional lids 3 are shown at both ends of the apparatus 1, which lids close internal spaces 2a accommodating containers 4. (See FIG. 1b)

FIG. 1b shows an overall view of the apparatus 1 in a section A-A. In this sectional view, the internal spaces 2a are shown, which accommodate the containers 4 including media (not shown). The functional lids 3 are closed by respective covers 3c. The handle 2 is supported by the adapter 5.

FIG. 2 shows an isometric exploded view of the apparatus 1. The containers 4 are inserted into the internal spaces 2a of the handle 2. The functional lids 4 close the internal spaces 2a. The adapter 5, together with the further receptacle 5a, is positioned at the pipe 6 and attached with the additional part 5b. The apparatus 1 is then inserted into the adapter 5 at the adapter receptacle 2c.

Figure 3:
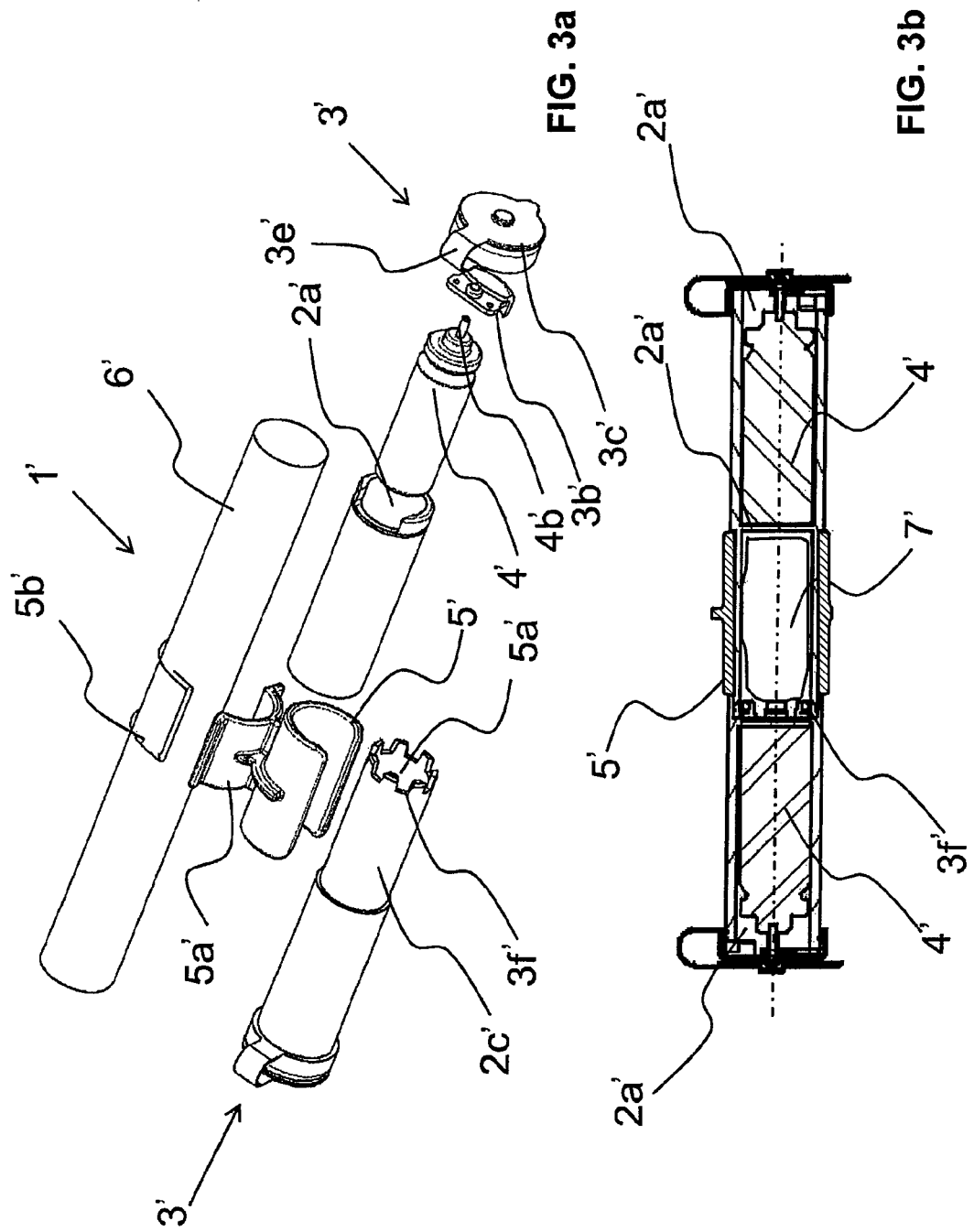

FIG. 3a shows an isometric exploded view of an emergency set 1'. The emergency set 1' is attached at the pipe 6' of, for example, a bicycle by means of the adapter 5'. The handle 2' can be divided at the level of the center internal space 2a' and is opened or closed by a fastener 3f. The outer internal spaces accommodate containers 4', in this case spraying bottles, which are actuated by the functional lid 3'.

FIG. 3b shows a sectional view of the emergency set 1'. In this illustration, the center internal space 2a' accommodates a safety vest 7'. Spraying bottles are disposed in the two outer internal spaces 2a'.

Figure 4:
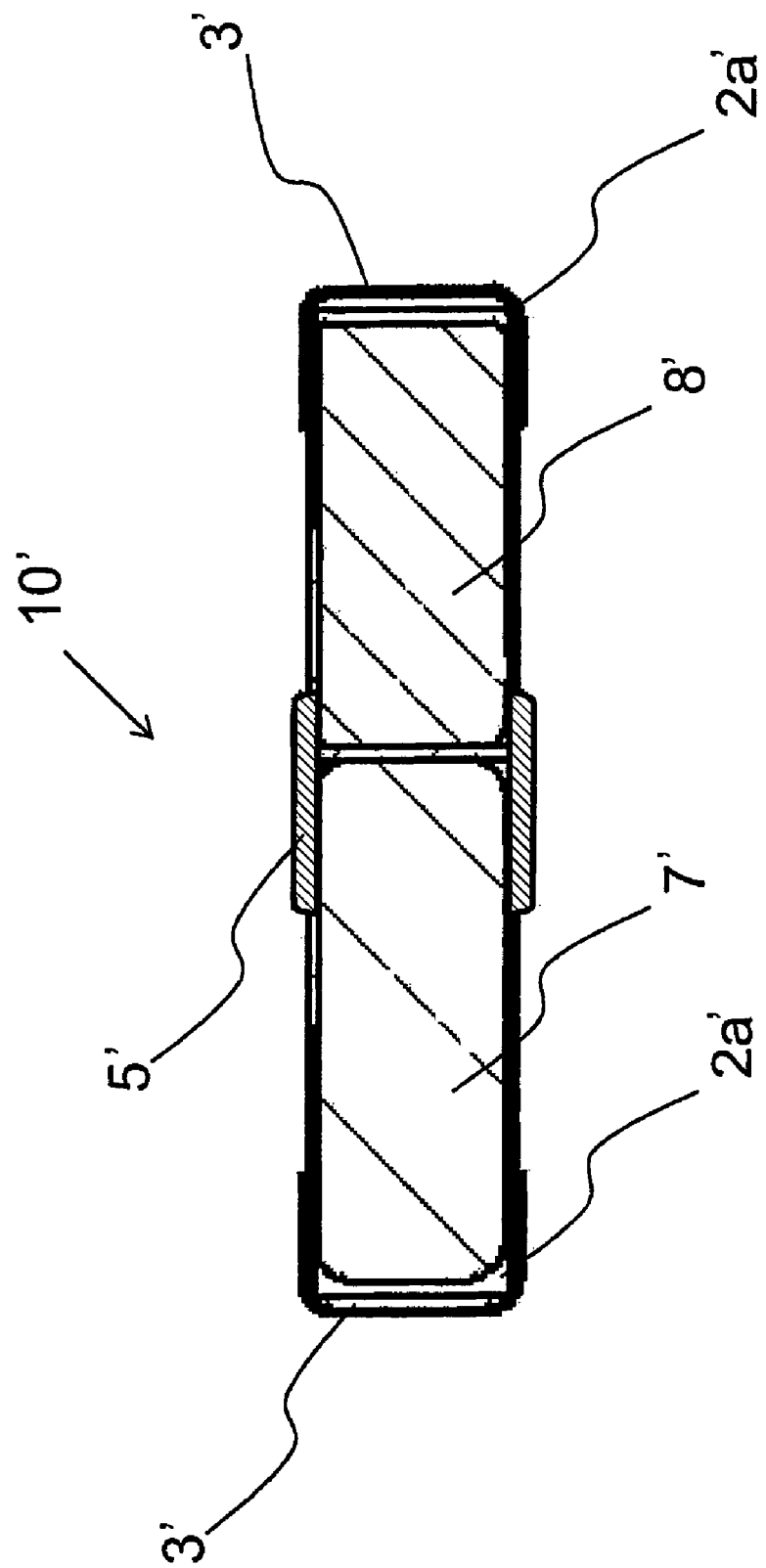
FIG. 4 is a sectional view of a knapsack.

FIG. 4 shows a sectional view of a knapsack 10'. Herein, it is shown how the internal spaces 2a' are closed by a simple lid 3'. In the internal spaces 2a', respectively a safety vest 7' and a gauze bandage 8' are disposed.

FIG. 5 shows an isometric illustration of the emergency set 1'. In this view, a possible arrangement on a bicycle is shown. The adapter 5' enables the accommodation of a drinking bottle 9', an emergency set 1' and a knapsack 10'.

Figure 6:
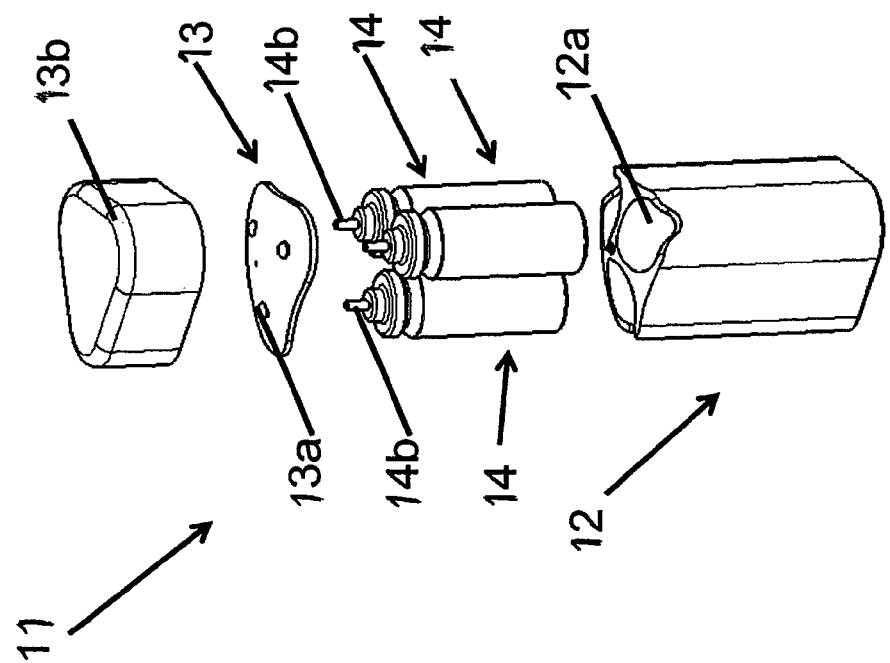
FIG. 6 is an isometric exploded view of a further embodiment of the apparatus in the form of an emergency set box.

FIG. 6 shows an isometric exploded view of an emergency set box 11. The shown emergency set box 11 comprises three internal spaces 12a. Three containers 14 are depicted, as they can be accommodated in these internal spaces 12a. A functional lid 13 comprises openings 13a through which the medium 14a (see FIG. 7) may escape from the containers 14. The cover 13b serves as a protection against contamination and is shown above the openings 13a.

Figure 7:
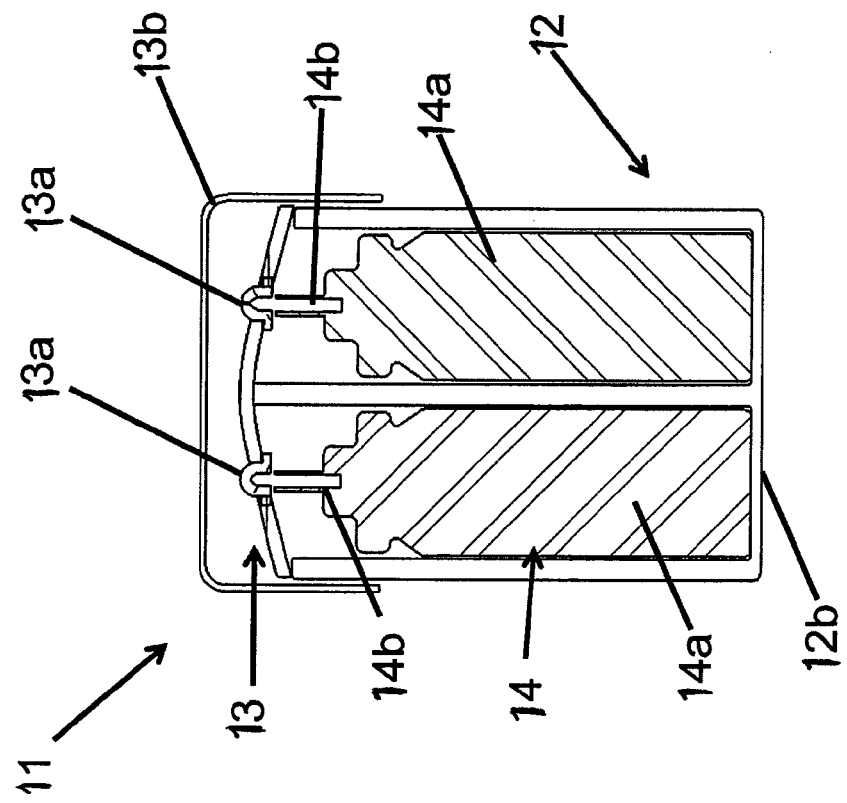
FIG. 7 is a sectional view of the emergency set box.

FIG. 7 shows a sectional view of the emergency set box 11. A possible arrangement is shown herein. The containers 14 are located in the internal spaces 12a.

The spray pins 14b of the containers 14 are arranged under the functional lid 13, such that the medium 14a may escape through the openings 13a when the functional lid 13 is actuated. The cover 13b closes the emergency set box 11 and protects it against contamination.

FIG. 8 shows a triangle shaped base body 12 of the inventive emergency set box 11. In this illustration, a possible shape of the base body is shown.

FIG. 9 shows a circular shaped base body 12 of the inventive emergency set box 11. In this illustration, a further possible shape of the base body 12 is shown.

FIG. 10 is a perspective view of a further embodiment of the apparatus 1, one cover 3c of which is shown in an open state.

FIG. 11 shows a sectional view of this embodiment of the apparatus 1, in which components corresponding to those of the preceding embodiments are designated with the same reference numerals. Accordingly, the apparatus 1 comprises a handle or a housing 2 which comprises, in this example, three housing parts 20, 21, 22 with respective internal spaces 20', 21' and 22'. The housing parts 20 and 21 are detachably connected through suitable connecting means 23, and the housing parts 21 and 22 are detachably connected through suitable connecting means 24. Examples for such connecting means are screw fittings, plug sockets or also bayonet couplings.

In the two internal spaces 20' and 22', containers for spraying agents, such as spray patches or cooling agents, are respectively arranged, which may also be referred to as cartridges.

The portion of the housing 2 surrounded with a circle B in FIG. 11 is shown enlarged in FIG. 12. From this illustration, it is shown that the functional lid 3 is provided with an opening 3a, wherein the functional lid 3 receives the spray pin 4b of the container 4 in a center recess 3f. As is made clear by FIG. 12, the spray pin 4b and its opening as well as the opening 3a are located on the longitudinal axis 2b of the housing 2, such that a spraying direction of the medium within the container 4 is aligned with respect to the longitudinal axis 2b when the functional lid 3 is actuated.

Further, the illustration of FIG. 12 makes clear that the lid or the cover 3c is pivotally connected to the housing 2 through a clip connection. Said clip connection comprises a bridge 16 fixed at the housing 2 and a fork-shaped bridge receptacle 15 attached at the lid 3c, which may be clipped onto the bridge 16 due to its elastic properties.

FIG. 13 shows a perspective view of a further embodiment of the inventive apparatus similar to FIG. 10, except that the cover or lid 3c of the embodiment of FIG. 10 is connected to the housing 2 through an integral hinge 3e.

FIG. 14 clarifies the structure illustrated in FIG. 11, wherein in this case only one cartridge 4 is arranged in the right-hand internal space 22'.

FIG. 15 in turn shows an enlarged illustration of detail C of FIG. 14.

From this illustration, it becomes clear that the embodiment according to FIGS. 13 to 15 enables a redirection of the spraying direction about 90° with respect to the longitudinal axis 2b. For this purpose, the cartridge or the container 4 comprises a lid 17 in which two spraying agent channels 18 and 19, arranged at right angles with each other, are provided. The spray pin 4b engages with the spraying agent channel 18 such that, upon actuation of the lid 17, the fluid jet escaping from the container 4 is redirected by 90° through the channels 18 and 19. The jet is ejected through a recess 120 in the housing 2, which is visible in FIG. 13.

In FIGS. 16 to 18, a further embodiment is shown, in which again all components corresponding to those of the preceding embodiments are designated with the same reference numerals.

Also in this embodiment, a redirection of the spraying direction by 90° with respect to the longitudinal axis 2b is provided. In this embodiment, two spraying agent channels 25 and 26, arranged at right angles with each other, are provided in the functional lid 3 for this purpose. In this case, the spray pin 4b engages with the spraying agent channel 25. If the functional lid 3 is actuated, e.g. by pressing onto its upper side, the spraying agent escapes through the spray pin 4b and is redirected through the perpendicularly arranged channels 25 and 26 and is ejected through the opening 27 of the spraying agent channel 26.

The invention was described with reference to a specific embodiment. It is, however, apparent that amendments and variations can be carried out without leaving the protective scope of the following claims. In this context, it has to be pointed out that all aforementioned embodiments and individual features can be combined with each other as desired.

In addition to the above written disclosure of the invention, it is explicitly referred to the drawings in FIGS. 1 to 18 for a completion thereof, with reference to the following list of Reference Numerals:

1 apparatus
2 handle/housing
2a internal space
2b longitudinal axis
2c adapter receptacle
3 functional lid
3a opening
3b lid insert
3d flap
3e integral hinge
3f recess
4 container/cartridge
4a medium
4b spray pin
5 adapter
5a further receptacle
5b additional part
6 pipe
1' emergency set
2' handle
2a' internal space
2b' longitudinal axis
2c' adapter receptacle
3' functional lid
3a' opening
3b' lid insert
3d' flap
3e' integral hinge
3f' fastener
4' container
4a' medium
3b' spray pin
5' adapter
5a' further receptacle
5b' additional part
6' pipe
7' safety vest
8' gauze bandage
9' drinking bottle
10' knapsack
11 emergency set box
12 base body
12a internal space
12b bottom
13 functional lid
13a opening
13b cover
14 container
14a medium
14b spray pin
14c emergency equipment 15 fork-shaped bridge receptacle
16 bridge
17 lid
18, 19 spraying agent channels/passages
20, 21, 22 housing part
20', 21', 22' internal spaces
23, 24 connecting means
25, 26 spraying agent channels/passages

The invention claimed is:

1. An apparatus for accommodating different exchangeable containers, each container having an actuatable spray pin for discharging contents of the container, the apparatus comprising:
    a body defining at least two separated and closable internal spaces, each internal space defining a longitudinal axis and adapted to receive one of the containers; and,
    a functional lid coupled to the body and closing one of the internal spaces, the functional lid including at least one spray-pin-receiving recess aligned with the longitudinal axis and positioned to receive and directly engage the spray pin when the one of the containers is received in the one of the internal spaces, the functional lid further including a channel having at least a portion aligned with the longitudinal axis and in direct fluid communication with the spray-pin-receiving recess for receiving and directing the contents of the container when the functional lid is actuated, and the functional lid further including an opening communicating with the channel and through which the contents of the container are expelled when the functional lid is actuated, wherein the functional lid is moveable with respect to the body to depress the spray pin and thereby expel the contents of the container through the channel and the opening.

2. The apparatus of claim 1, wherein the functional lid includes a lid insert.

3. The apparatus of claim 1, further comprising a cover for closing the functional lid.

4. The apparatus of claim 3, wherein the functional lid is movably connected to the cover.

5. The apparatus of claim 1, wherein the body includes an adapter receptacle for attachment of an adapter.

6. The apparatus of claim 5, wherein the adapter includes a further receptacle.

7. The apparatus of claim 1, wherein the at least two separated and closable internal spaces includes three separated and closable internal spaces, wherein the longitudinal axis is a common longitudinal axis such that the three separated and closable internal spaces are arranged on the common longitudinal axis, and wherein the body can be opened and closed for access to a central internal space by a fastener.

8. The apparatus of claim 7, wherein the fastener is formed as a thread or a clip.

9. The apparatus of claim 7, wherein a safety vest is disposed in the central internal space.

10. The apparatus of claim 7, wherein a gauze bandage is disposed in the central internal space.

11. The apparatus of claim 7, further comprising an adapter attached to the body and to a knapsack.

12. The apparatus of claim 11, wherein the adapter also attaches to a drinking bottle.

13. The apparatus of claim 1, wherein the internal spaces are arranged on a common longitudinal axis.

14. The apparatus of claim 1, wherein the internal spaces are arranged side-by-side.

15. The apparatus of claim 1, wherein the functional lid is a first functional lid and closes a first one of the at least two separated and closeable internal spaces, the apparatus further comprising a second functional lid coupled to the body and closing a second one of the internal spaces.

16. The apparatus of claim 1, wherein the entire channel and the opening are aligned with the longitudinal axis.

17. The apparatus of claim 1, wherein a first portion of the channel is aligned with the longitudinal axis, and wherein a second portion of the channel is arranged at a right angle with respect to the first portion of the channel.

* * * * *